US007569058B2

(12) United States Patent
Zwirnmann

(10) Patent No.: US 7,569,058 B2
(45) Date of Patent: Aug. 4, 2009

(54) ADJUSTABLE LENGTH TAP AND METHOD FOR DRILLING AND TAPPING A BORE IN BONE

(75) Inventor: Ralph Fritz Zwirnmann, Roslyn, PA (US)

(73) Assignee: Synthes USA, LLC, West Chester, PA (US)

( * ) Notice: Subject to any disclaimer, the term of this patent is extended or adjusted under 35 U.S.C. 154(b) by 530 days.

(21) Appl. No.: 11/221,546

(22) Filed: Sep. 7, 2005

(65) Prior Publication Data

US 2006/0004372 A1    Jan. 5, 2006

Related U.S. Application Data

(62) Division of application No. 10/292,515, filed on Nov. 13, 2002, now Pat. No. 6,951,562.

(51) Int. Cl.
    *A61B 17/16* (2006.01)
(52) U.S. Cl. ....................................................... 606/80
(58) Field of Classification Search .................. 606/80, 606/79, 87, 96; 408/202, 203, 241 S
    See application file for complete search history.

(56) References Cited

U.S. PATENT DOCUMENTS

| 412,952 A | 10/1889 | Elterich |
| 532,472 A | 1/1895 | Minnich |
| 2,344,143 A | 3/1944 | Harding |
| 3,301,101 A | 1/1967 | McEwen |
| 3,576,076 A | 4/1971 | Weissman |
| 3,855,705 A | 12/1974 | Malmin |
| 4,010,737 A | 3/1977 | Vilaghy et al. |
| 4,039,266 A | 8/1977 | O'Connell |
| 4,142,517 A | 3/1979 | Stavropoulous et al. |

(Continued)

FOREIGN PATENT DOCUMENTS

DE    38 00 482    7/1989

(Continued)

OTHER PUBLICATIONS

W. Lorenz Surgical, Selected Articles & Instrumentation, 2000.

(Continued)

*Primary Examiner*—Eduardo C Robert
*Assistant Examiner*—David Comstock
(74) *Attorney, Agent, or Firm*—Schwegman, Lundberg & Woessner, P.A.

(57) ABSTRACT

The present invention is directed to an adjustable self drilling tap assembly and method for drilling and tapping bores in bone for use in orthopedic procedures to treat bone. The adjustable length tap assembly includes a shaft having cutting threads for drilling holes in bone, a stop collar configured and dimensioned to be translatable along the longitudinal axis of the shaft, and a locking collar comprising a member configured and dimensioned to be received over at least a portion of the stop collar. The locking collar preferably is configured and dimensioned to engage with the stop collar to adjustably set the effective length for the cutting threads and to prevent movement of the stop collar along the longitudinal axis of the shaft.

24 Claims, 12 Drawing Sheets

U.S. PATENT DOCUMENTS

| | | | |
|---|---|---|---|
| 4,341,206 A * | 7/1982 | Perrett et al. | 606/80 |
| 4,521,144 A | 6/1985 | Ginter | |
| 4,521,145 A | 6/1985 | Bieler | |
| 4,549,538 A | 10/1985 | Schadrack, III et al. | |
| 4,552,370 A | 11/1985 | Baumgartner | |
| 4,580,933 A | 4/1986 | Wilkins | |
| 4,637,539 A | 1/1987 | Turcott et al. | |
| 4,693,656 A | 9/1987 | Guthrie | |
| 4,710,075 A | 12/1987 | Davison | |
| 4,877,359 A | 10/1989 | Kolacek | |
| 4,978,261 A | 12/1990 | Wright, III | |
| 4,998,881 A | 3/1991 | Lauks | |
| 5,051,043 A | 9/1991 | Spitznagel | |
| 5,051,092 A | 9/1991 | Miller | |
| 5,078,552 A | 1/1992 | Albel | |
| 5,180,388 A | 1/1993 | DiCarlo | |
| 5,190,548 A | 3/1993 | Davis | |
| 5,382,120 A | 1/1995 | Parsons | |
| 5,382,250 A | 1/1995 | Kraus | |
| 5,409,490 A | 4/1995 | Ethridge | |
| 5,423,824 A | 6/1995 | Akerfeldt et al. | |
| 5,520,692 A | 5/1996 | Ferrante | |
| 5,591,207 A | 1/1997 | Coleman | |
| 5,634,927 A | 6/1997 | Houston et al. | |
| 5,669,915 A | 9/1997 | Caspar et al. | |
| 5,741,267 A | 4/1998 | Jorneus et al. | |
| 5,782,835 A | 7/1998 | Hart et al. | |
| 5,785,522 A | 7/1998 | Bergstrom et al. | |
| 5,795,110 A | 8/1998 | Wirth, Jr. et al. | |
| 5,810,826 A | 9/1998 | Akerfeldt et al. | |
| 5,810,828 A | 9/1998 | Lightman et al. | |
| 5,823,720 A | 10/1998 | Moore | |
| 5,890,897 A | 4/1999 | Kruger et al. | |
| 5,895,389 A | 4/1999 | Schenk et al. | |
| 5,941,706 A | 8/1999 | Ura | |
| 6,015,411 A | 1/2000 | Ohkoshi et al. | |
| 6,017,348 A | 1/2000 | Hart et al. | |
| 6,110,178 A | 8/2000 | Zech et al. | |
| 6,120,506 A | 9/2000 | Kohrs et al. | |
| 6,235,035 B1 | 5/2001 | Boukhris | |
| 6,283,966 B1 * | 9/2001 | Houfburg | 606/914 |
| 6,287,313 B1 | 9/2001 | Sasso | |
| 6,306,142 B1 | 10/2001 | Johanson et al. | |
| 6,383,190 B1 | 5/2002 | Preissman | |
| 6,951,562 B2 | 10/2005 | Zwirnmann | |

FOREIGN PATENT DOCUMENTS

| | | |
|---|---|---|
| JP | 03-085179 | 4/1991 |
| JP | 04-221538 | 8/1992 |
| JP | 07-313586 | 12/1995 |
| JP | 08-024347 | 1/1996 |
| JP | 09-201330 | 8/1997 |
| WO | WO-01/32100 A2 | 5/2001 |

OTHER PUBLICATIONS

Stryker Leibinger, Delta System Resorbable Implant Technology, No Date.

"International Application Serial No. PCT/US03/36619, International Search Report mailed Apr. 7, 2004", 4 pgs.

"U.S. Appl. No. 10/292,515, Advisory Action mailed Jan. 11, 2005", 3 pgs.

"U.S. Appl. No. 10/292,515, Final Office Action mailed Oct. 15, 2004", 6 pgs.

"U.S. Appl. No. 10/292,515, Non-Final Office Action mailed May 26, 2004", 5 pgs.

"U.S. Appl. No. 10/292,515, Notice of Allowance mailed May 25, 2005", 6 pgs.

"U.S. Appl. No. 10/292,515, Response filed Sep. 20, 2004 to Non-Final Office Action mailed May 26, 2004", 9 pgs.

"U.S. Appl. No. 10/292,515, Response filed Apr. 22, 2004 to Restriction Requirement mailed Mar. 31, 2004", 1 pg.

"U.S. Appl. No. 10/292,515, Restriction Requirement mailed Mar. 31, 2004", 4 pgs.

"U.S. Appl. No. 10/292,515, Amendment filed Dec. 13, 2004 to Final Office Action mailed Oct. 15, 2004", 10 pgs.

"Chinese Application No. 200380107183.7, First Office Action mailed Feb. 2, 2007", (w/ English Translation), 8 pgs.

"Chinese Application No. 200380107183.7, Response filed Nov. 13, 2007 to Second Office Action mailed Sep. 27, 2007", (w/ English Translation), 21 pgs.

"Chinese Application No. 200380107183.7, Response filed Jun. 14, 2007 to First Office Action mailed Feb. 2, 2007", 6 pgs.

"Chinese Application No. 200380107183.7, Second Office Action mailed Sep. 27, 2007", (w/ English Translation), 8 pgs.

"European Patent Application No. 04750971.6, Communication mailed Jun. 12, 2008", 5 pgs.

"Japanese Application No. 2002-506661, Notice of the Reason for the Rejection mailed Feb. 27, 2008", (w/ English Translation), 7 pgs.

"Japanese Application No. 2002-506661, Official Notice of Reason for the Final Rejection mailed Jul. 11, 2008", (w/ English Translation), 4 pgs.

Kaneko, Y., et al., "Synthesis and Swelling—deswelling kinetics of poly(*N*-isopropylacrylamide) hydrogels grafted with LCST modulated polymers", *Journal of Biomaterials Science, Polymer Edition*, 10(11), (1999),1079-1091.

Stile, R. A., et al., "Synthesis and Characterization of Injectable Poly(*N*-isopropylacrylamide)-Based Hydrogels That Support Tissue Formation in Vitro", *Macromolecules*, 32, (1999), 7370-7379.

* cited by examiner

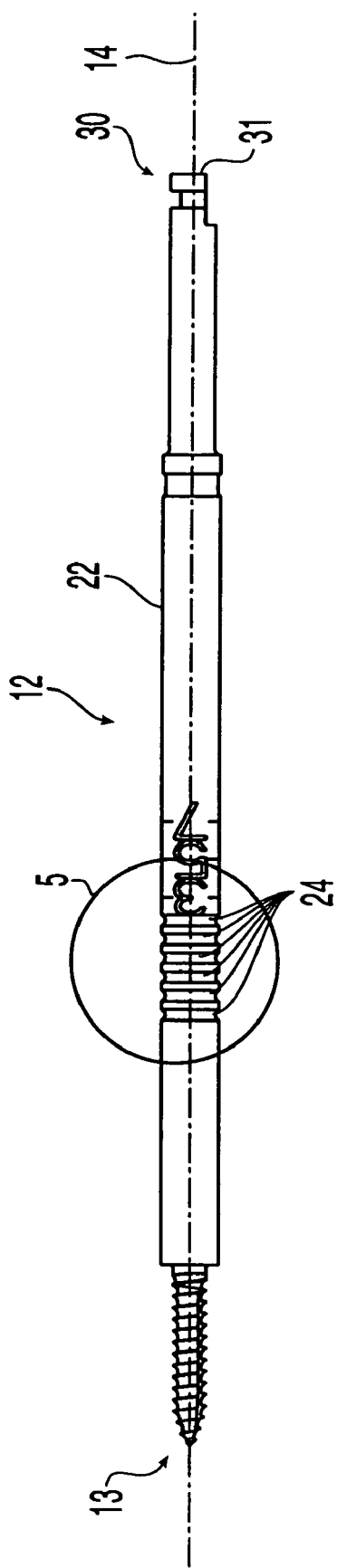
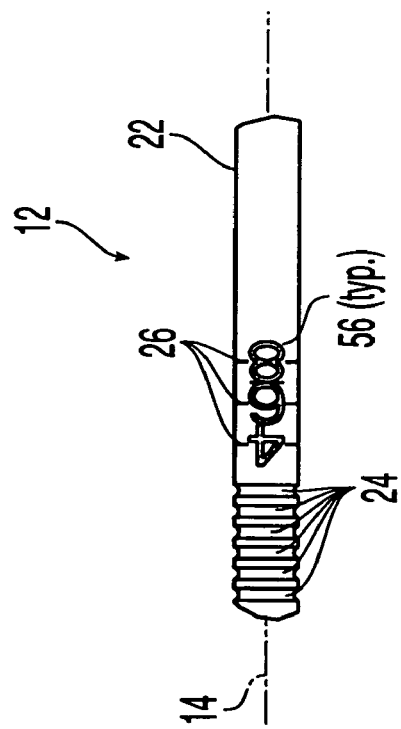
Fig. 3
Fig. 4

ADJUSTABLE LENGTH TAP AND METHOD FOR DRILLING AND TAPPING A BORE IN BONE

CROSS-REFERENCE TO RELATED APPLICATIONS

This is a divisional of U.S. patent application Ser. No. 10/292,515 filed Nov. 13, 2002 now U.S. Pat. No. 6,951,562, entitled "Adjustable Length Tap and Method for Drilling and Tapping a Bore in Bone," which is incorporated herein by reference in its entirety.

FIELD OF THE INVENTION

The present invention is directed to a self-drilling tap and its method for use in orthopedic procedures to treat bone, and in particular to a device and method for drilling and tapping holes in bone to accommodate screws used in cranio-facial, mandible, pelvic and other orthopedic procedures.

BACKGROUND OF THE INVENTION

Drilling in bones, particularly bones of the face and head, requires accurate and reliable control over the penetration depth. For instance, over drilling and tapping a bore may damage the brain or other underlying soft tissue. To reduce this risk, self-drilling taps for use in cranio-facial procedures generally have a fixed depth. There exists a need for a self-drilling tap having an adjustable length, which may accurately and reliably replace several taps of various fixed lengths.

SUMMARY OF THE INVENTION

The present invention is directed to a tap assembly which may be adjusted by a user to drill and tap holes in bone in order to accommodate screws of various lengths. The adjustable length tap may comprise a shaft, a stop collar and a locking collar, which cooperate to expose and set an effective length of cutting threads located on the tip of the shaft.

The shaft preferably has a longitudinal axis, a proximal end, and a distal end with cutting threads for drilling and tapping holes in bone. The adjustable length tap assembly may also include a stop collar having proximal and distal ends. The distal end of the stop collar is preferably configured and dimensioned to provide a stop for the self drilling tap. The stop collar preferably is configured and dimensioned to be translatable along the longitudinal axis of the shaft. The shaft preferably includes length indicator marks, the length indicator marks being configured and dimensioned to allow for a controlled setting of the effective length of the adjustable length tap assembly. Each length indicator mark is preferably configured and dimensioned to correspond with one effective length. In addition, each length indicator mark is preferably configured and dimensioned to be visibly aligned with the proximal end of the stop collar, when the effective length is set. In an exemplary embodiment, each length indicator mark is selectively disposed on the shaft, and each length indicator mark is visibly identified by indicia. The shaft is preferably made from bio-compatible materials and may be made from non-magnetic materials.

The stop collar has a body having an inner surface and an outer surface. A portion of the inner surface is preferably configured and dimensioned to engage with the shaft in at least one predetermined location. The stop collar preferably has one or more fingers, and the shaft preferably has one or more grooves. In addition, the one or more fingers may have inner and outer surfaces and at least one projection or nub formed on the inner surface. The projection preferably is configured and dimensioned to interact with the grooves to prevent translational movement of the stop collar along the longitudinal axis of the shaft. The one or more fingers preferably is formed by at least two slots. Each of the two slots preferably extend from the outer surface of the stop collar to the inner surface of the stop collar. Preferably, the stop collar has at least two fingers, the fingers being substantially identical and arranged in a substantially symmetrical configuration about a central axis of the stop collar.

In an illustrative embodiment, the at least one projection on the stop collar has a mid-point, and the at least one groove on the shaft has a mid-point. A first distance measured from the mid-point of the at least one projection to the proximal end of the stop collar preferably is related to a second distance measured from the mid-point of the at least one groove to a corresponding length indicator mark on the shaft. The first distance preferably is substantially equal to the second distance. The grooves preferably extend continuously about the shaft, and the grooves preferably are oriented substantially perpendicular to the longitudinal axis of the shaft. In an exemplary embodiment, the grooves are substantially equidistant from one another. The grooves may also be substantially identical in size and shape.

The adjustable length tap assembly also comprises a locking collar. The locking collar preferably is configured and dimensioned to be received over at least a portion of the stop collar. The locking collar is preferably configured and dimensioned to engage with the stop collar to set the effective length of the cutting threads, and preferably to prevent movement of the stop collar along the longitudinal axis of the shaft. The locking collar, also, is preferably configured and dimensioned to bear against a structure on the outer surface of the one or more fingers to releasably engage the at least one nub with a groove on the shaft. The locking collar preferably comprises a tubular member having a bore, and the proximal end of the locking collar preferably is capable of translating over the proximal end of the stop collar. In an exemplary embodiment, at least a part of the locking collar is transparent, and the locking collar preferably is formed from a medical grade poly-carbonate.

In use, the locking collar and the stop collar preferably engage or mate with each other in at least two configurations, a first configuration which allows transnational movement of the stop collar and locking collar together along the shaft, and a second configuration that prevents translational movement of the stop collar along the longitudinal axis of the shaft. The stop collar and locking collar, generally, are free to rotate about the shaft when the stop collar and locking collar engage in the second configuration.

The present invention is also directed to a surgical kit for drilling and tapping holes in bone. The kit preferably comprises one or more shafts each having a longitudinal axis, a proximal end and a distal end. At least a portion of each shaft should have cutting threads for drilling and tapping bores in bone. The kit may also include a stop collar having proximal and distal ends, which preferably is configured and dimensioned to be translatable along the longitudinal axis of each of the shafts. The stop collar preferably has a body having an inner surface and an outer surface, at least a portion of the inner surface being configured and dimensioned to engage with the at least one shaft in at least one predetermined location. Additionally, the kit may further include include a locking collar comprising a member configured and dimensioned to be received over at least a portion of the stop collar. The locking collar preferably is configured and dimensioned to engage or mate with the stop collar to set at least one effective length for the cutting threads and preferably to prevent movement of the stop collar along the longitudinal axis of the at least one shaft.

The invention also relates to a method for drilling and tapping a bore in bone. The method preferably comprises selecting a bone fastening element having a screw thread, and selecting a self-drilling tap having a longitudinal axis and cutting threads. Preferably, the cutting threads are located on the distal end of the self-drilling tap and are adapted to create and tap a bore in bone for receiving the selected screw thread. The method preferably includes mounting a stop collar on the tap, positioning a locking collar on the tap, passing at least a part of the locking collar over the proximal end of the stop collar, and joining the stop collar with the locking collar. The method preferably comprises positioning the stop collar in at least one predetermined location which may cover at least a part of the cutting threads, verifying the location of the stop collar by visually inspecting the location of the proximal end of the stop collar relative to the self-drilling tap, and locking relative movement of the self-drilling tap, stop collar, and locking collar along the longitudinal axis. The method preferably includes placing the cutting threads on bone, rotating the self-drilling tap to advance the cutting threads into bone, forming a tapped bore in bone, contacting the stop collar against a surface to block advancement of the self drilling tap, and removing the self-drilling tap from the bore. The method may further include advancing the screw thread into the bore to fix the bone fastening element in bone.

BRIEF DESCRIPTION OF THE DRAWINGS

Preferred features of the present invention are disclosed in the accompanying drawings, wherein similar reference characters denote similar elements throughout the several views, and wherein:

FIG. 3 shows a plan view of the shaft of the tap assembly of FIG. 2;

FIG. 4 shows a partial plan view of the reverse side of the of shaft of FIG. 3;

DETAILED DESCRIPTION OF THE EMBODIMENTS

In the description that follows, any reference to either orientation or direction is intended primarily for the convenience of description and is not intended in any way to limit the scope of the present invention thereto.

Figure 1:
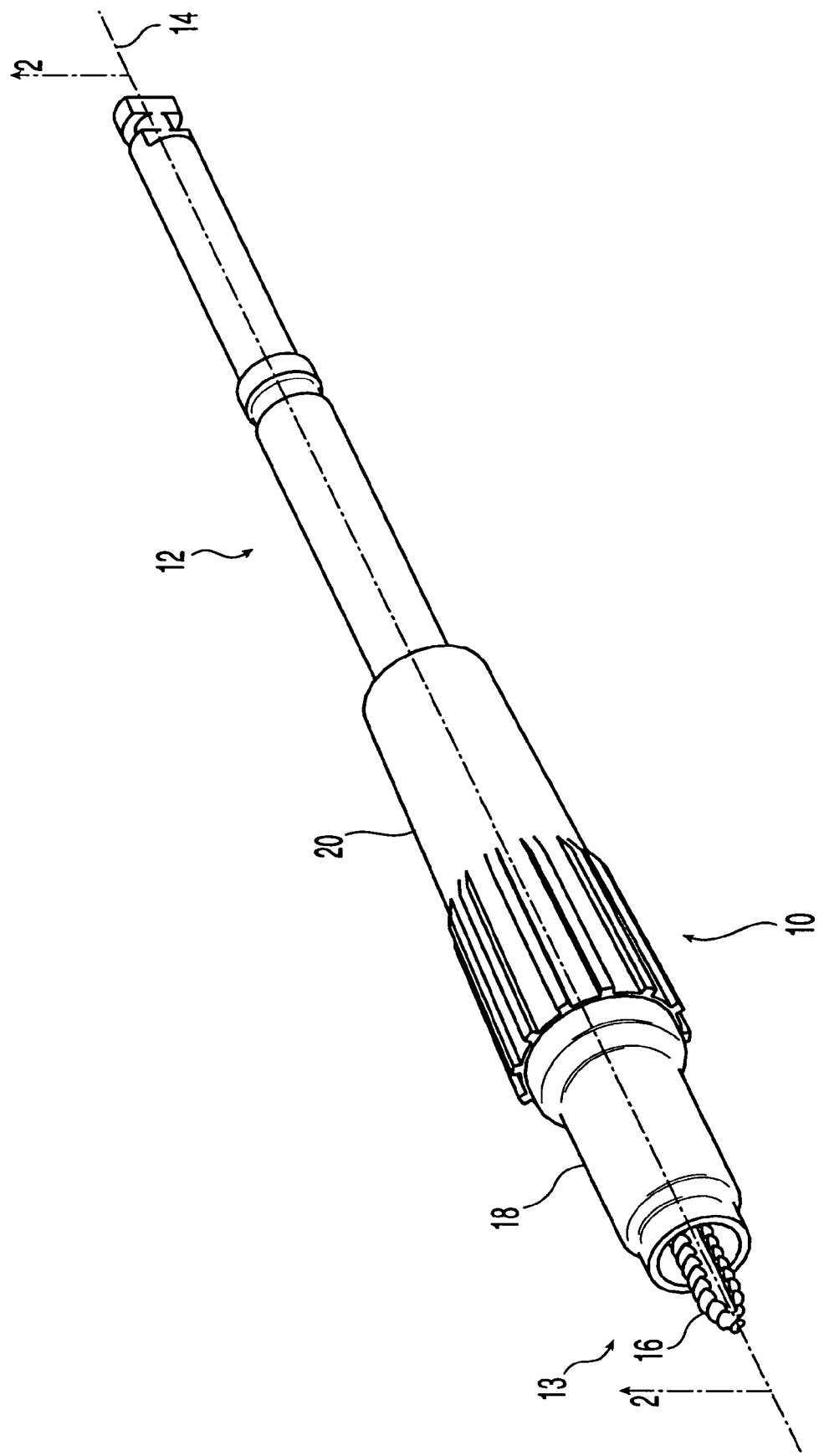
FIG. 1 shows a perspective view of an exemplary embodiment of the adjustable length tap assembly.

FIG. 1 shows an assembly 10 for use in drilling and tapping holes in bone. The assembly 10 comprises a self-drilling tap 12 having a longitudinal axis 14, a stop collar 18, and a locking collar 20. The self-drilling tap 12 may have a distal end 13 with cutting threads 16 adapted to drill and tap holes in bone. The stop collar 18 and locking collar 20 may be moved along the self-drilling tap 12 to expose a portion of the cutting threads 16. The relative position of stop collar 18 and locking collar 20 may be fixed along the longitudinal axis 14 of the self-drilling tap 12. The stop collar 18 and the locking collar 20 may be free to rotate about the longitudinal axis 14 of the self-drilling tap, even though translational movement along the longitudinal axis 14 is prevented. The assembly 10 may be used with other instruments such as a handle and guide plate (not shown) to drill and tap holes in bone. Detachable handles, guide plates, and drills are representative of the instruments and other devices that may be used in conjunction with the adjustable length tap assembly. These instruments, however, may not always be required or may be replaced by different devices that perform similar, additional, or different functions.

Figure 2:
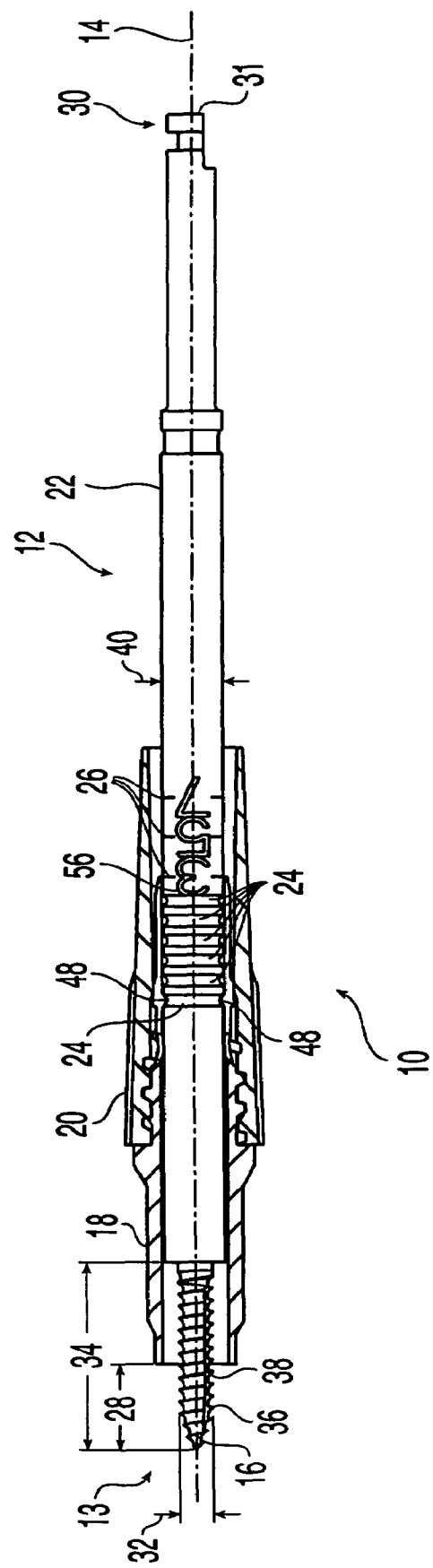
FIG. 2 shows a partial cross-sectional view along line 2-2 of FIG. 1.

FIG. 2 shows a cut away view of the adjustable length tap assembly. The stop collar 18 and the locking collar 20 are shown in cross-section, and the shaft 22 is shown in plan view. As shown in FIG. 2, the self-drilling tap 12 includes a shaft 22 having a tip or distal end 13 with cutting threads 16. The tap 12 further comprises a plurality of circumferential grooves 24, indica 26, such as for example lines, for marking the effective length 28 of the exposed portion of the cutting threads 16, and a coupling element 30 for connecting the self-drilling tap 12 to a handle or a drill (not shown) at the proximal end 31 thereof.

The maximum outer diameter 32 of the cutting threads 16 and the length 34 of the tip 13, which contains the cutting threads, may be fixed. The dimensions of the tip 13, for any particular tap 12, may be based on the size and length of the screw for to be inserted in the bore. The dimensions of the tip 13 may further be adapted to accommodate the thickness of a guide plate. For instance, a special screw may be developed for use in a pelvic procedure, for example, and the dimensions of the tip 13 of the self-drilling tap 12 may be designed to accommodate that screw. For example, one screw type may have an outer diameter of 1.5 mm and a length of 3 mm, and the dimension of the tip 13 may be configured and dimensioned to create a tapped bore that is adapted for screws of that type. Other non-limiting examples of screws, for which the self-drilling tap 12 may be dimensioned, include screws having an outer diameter from about 2.0 mm to about 4.0 mm and having a length from about 3.0 mm to about 8.0 mm. As one skilled in the art would readily appreciate, a self-drilling tap may also be developed for larger or smaller screws.

The cutting threads 16 may be particularly adapted to cut and remove bone without damaging adjacent tissue. The threads may include sharp cutting flutes 36 and one or more straight flutes 38 for removing bone chips and cuttings from the bore. For example, two straight flutes aligned 180° from each other may be disposed on the tip. One of ordinary skill in the art would readily appreciate that the number and configuration of cutting flutes 36 and straight flutes 38 may be widely varied, or in addition to or alternatively a wide variety of other configurations and combinations may be used.

The shaft 22 of the tap 12, preferably, may have an outer diameter 40 that is operably configured and dimensioned to slidably receive the stop collar 18 and the locking collar 20. A set of taps which may be adapted for screws having differing predetermined diameters and lengths, preferably may each have a shaft 22 of same diameter 40. In an exemplary embodiment, the outer diameter 40 of the shaft 22 may be about 3.0 mm. As one skilled in the art would readily appreciate, a set of self-drilling taps having different tip configurations may be supplied as a kit for use with one stop collar 18 and one locking collar 20. More than one stop collar 18 and more than one locking collar may also be supplied in the kit. For example, a set of taps 12 having a different outer diameter may be supplied which would be used with different stop and locking collar combinations.

Figure 5:
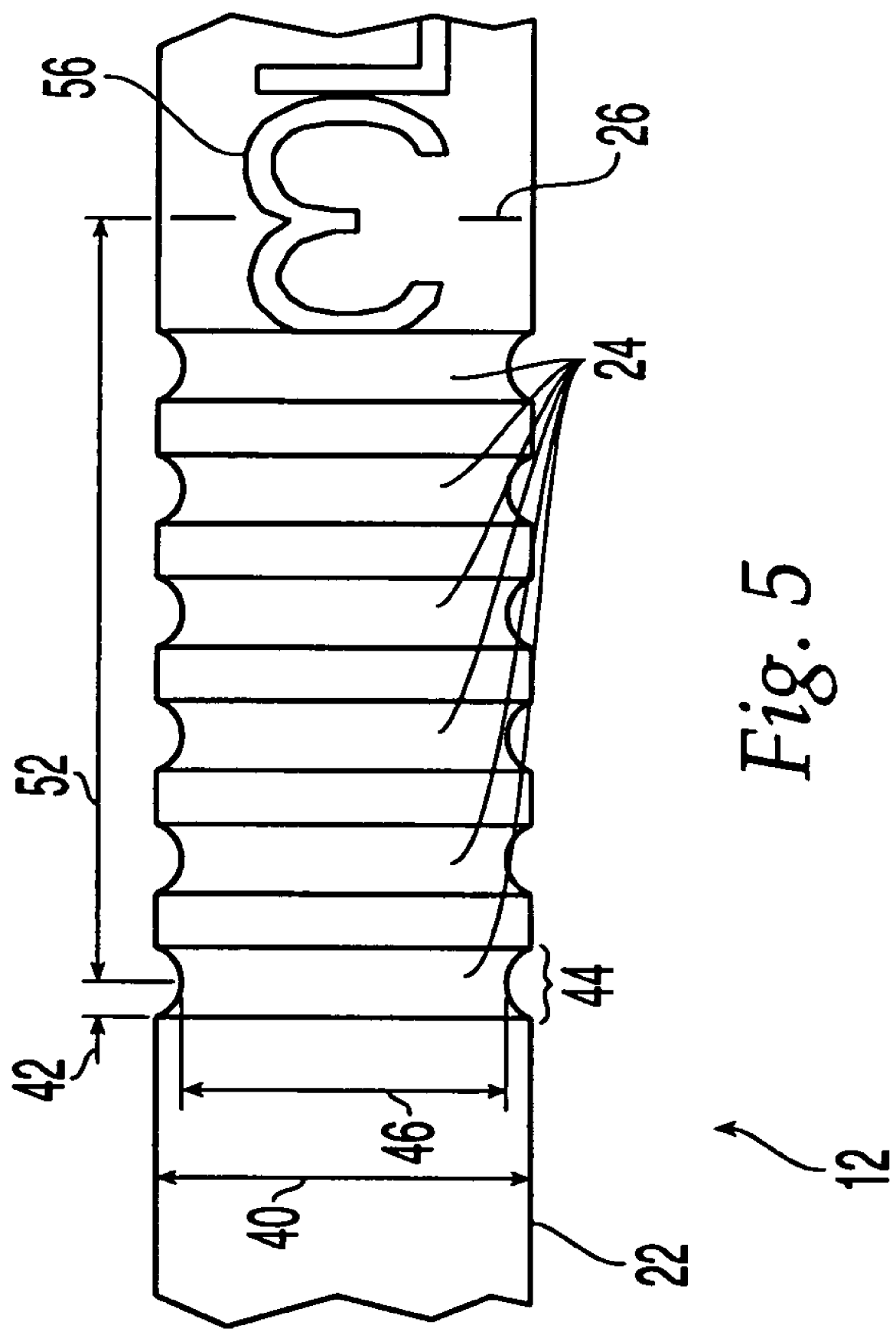
FIG. 5 shows an enlarged view of grooves and markings on the shaft of FIG. 3.

Referring to FIGS. 3-5, the shaft 22 may further comprise two or more grooves 24. The grooves 24 may be spaced from the tip 13 on the middle portion of the tap 12. Each groove 24 may or may not extend continuously about the shaft 22. In an illustrative embodiment of a self-drilling tap 12 there may be six grooves 24 spaced equidistant from one another and oriented perpendicular to the longitudinal axis of the shaft 22. As shown in FIG. 5, the radius 42 (i.e, the distance equal to one-half the groove width 44) of each groove 24 preferably may be substantially constant. In addition, each groove preferably may have substantially the same radius 42. Similarly, the diameter 46 of the grooves 24 may vary, but in a preferred embodiment are the same. The radius 42 and diameter 46 of each groove 24 may be operably configured and dimensioned to cooperate with at least one detent or nub 48 on the stop collar 18, as shown in FIG. 2. Engagement of a nub or projection 48 with a groove 24 may be used to set the position of the stop collar along the length of the shaft 22 and thus set the penetration or effective length 28 of the adjustable tap assembly 10. As described in further detail below, a user may selectively press the nubs of the stop collar 18 into a groove 24 on the shaft to lock the penetration or effective length 28 of the adjustable tap assembly.

As shown in FIG. 5, a tap 12 having a shaft 22, for example, with an outer diameter 40 of about 3.0 mm may have grooves 24 having a diameter 46 of about 2.6 mm and a radius 42 of about 0.3 mm. Each groove 24 may be spaced one from another at a fixed interval, for example, 1.0 mm on center. As one skilled in the art would readily appreciate, other groove configurations may be desirable. In general, however, a set of self-drilling taps adapted for screws of different diameters, as previously described, may have substantially identical grooves and groove patterns so as to provide the user of the tool with a uniform feel when setting the penetration or effective length 28 of the adjustable tap assembly 10. A standard feel for setting the effective length 28 of the adjustable tap assembly 10 may promote ease, reliability, and accuracy in the selection of a desired effective tap length 28 during a surgical procedure.

Indica 26 or length indicators may be marked on the shaft 22 perpendicular to the longitudinal axis 14 of the self-drilling tap 12. In general, one length indicator 26 may be marked on the shaft 22 for each groove 24. Each length indicator 26 may indicate the length of the screw for which a bore is to be drilled. Alternatively, the length indicator 26 may correspond to some other designation for a particular screw type. In general, the distance between the mid-point of one groove 24 and a corresponding length indicator 26 may correspond with the dimensions of the stop collar 18 to allow for the controlled and accurate setting of a predetermined tap length 28. For example, the distance 52 between the mid-point of a groove 24 and a corresponding length indicator 26, may be the same length as the distance 73, shown in FIG. 7, which is measured between the mid-point of the nub 48 and the end 54 of the stop collar.

Referring back to FIGS. 2-5, length indicators 26 may be selectively marked on the shaft 22. For instance, the length indicators for screws having odd number designations may be marked on one side of the shaft, and length indicators for screws having even number designations may be marked on the other side of the shaft. Such a marking pattern may facilitate the selection of a desired effective length 28 by making it easier to identify, select, and confirm the adjustment. Moreover, each length indicator 26 may be identified by indica 56 which uniquely signify each possible tap length 28 selection. For instance, the indica 56 may comprise numerals which relate to the length or type of screw for which a bore is to be drilled and tapped. In an illustrative configuration, the indica 56 may be numerals which are bisected by the associated length indicators 26. This configuration may provide for larger numerals and clearer identification of the associated length indicator. Markings 26, 56 may be laser etched into the shaft.

The self-drilling tap 12 may be adapted for use with an integrally formed handle (not shown). Alternatively, the proximal end of the self-drilling tap 31 may be adapted for connection to a removable handle or drill (not shown). For instance, the self-drilling tap 12 may have a hex coupling for connecting to a handle for use as a manually operated instrument. The tap 12 might also be adapted for quick coupling to a drill. In general, the tap may be made from materials which are bio-compatible and possess relatively high mechanical durability. For example, the tap may be integrally formed from a blank made from stainless steel. In a preferred embodiment, the tap may be made from 440A stainless steel. The tap may also be made from non-magnetic materials so that it may be suitable for use with an MRI system. The tap may also be radiolucent, or portions may be radiolucent.

Figure 6:
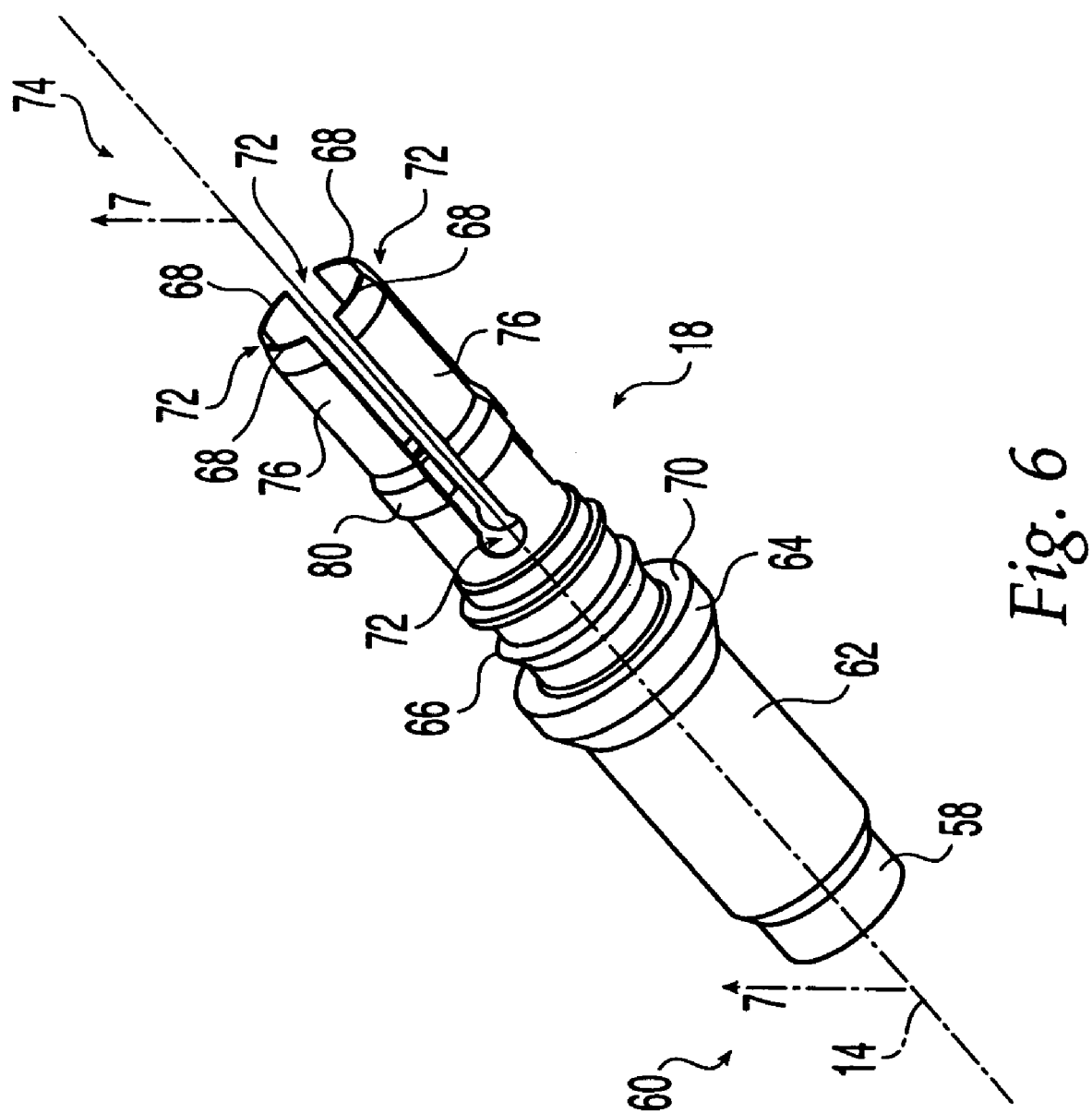
FIG. 6 shows a perspective view of the stop collar of the tap assembly of FIG. 1.

FIG. 6 shows a perspective view of the stop collar of FIG. 1. As previously described, the stop collar 18 is operably configured and dimensioned to cooperate with the shaft 22 and locking collar 20 to set and fix the penetration or effective length 28 of the adjustable length tap assembly 10. The stop collar shown in FIG. 6 has a nose 58 at the distal end 60, a fore-collar 62 adjacent the nose 58, an abutment ring 64, connecting elements 66 for coupling with the locking collar 20, and a plurality of fingers 68 for engaging with the shaft 20.

The nose 58 may be configured and dimensioned to provide a secure stop for the self-drilling tap 13 and may have an outer dimension close to the dimensions of the shaft to reduce visual obstruction of the tip 13 when the adjustable length tap assembly 10 is positioned for drilling. The outer dimension of the stop collar may then flare outward gradually to a second or intermediate outer-dimension at the fore-collar 62 to provide a surface which may be readily gripped and manipulated by a user. Thus, the profile of nose 58 and fore-collar 62 may be configured and dimensioned to reduce the likelihood of incorrect seating of the adjustable length tap assembly 10 on a drill plate and/or bone.

The fore-collar 62 may further include a transition to a portion having a larger outer dimension which may form an abutment ring 64. The abutment ring 64 may be operably configured and dimensioned to provide a stop 70 for the locking collar 20, which may be connected to the stop collar 18 by connecting elements 66 located near the abutment ring

64. In FIG. 6, the connecting elements 66 comprise external threads which are disposed about the central portion of the stop collar 18 between the abutment ring 64 and a plurality of fingers 68. Coupling elements other than threads may be used to couple the locking collar 20 with the stop collar 18.

The fingers 68 assist in fixing the position of the stop collar and may each generally comprise an elongated member, that is formed by slots 72 in a thin wall section of the stop collar 18. The fingers 68 are configured and dimensioned to flex. In FIG. 6, the stop collar 18 has four fingers 68. As one of skill in the art might appreciate, a stop collar 18 having a configuration with less or more fingers 68 might also be used. For example, a stop collar having three fingers defined by three slots may be used, or a stop collar with five fingers and having five slots may be used. The fingers 68 may be substantially identical in construction or they may differ one from another. Similarly, the fingers 68 may be disposed in a substantially symmetrical configuration or they may be disposed about the stop collar in some other fashion. For instance, in the embodiment shown in FIGS. 6-9, the stop collar 18 comprises four substantially identical fingers 68 disposed in a generally symmetrical pattern about the proximal end 74 of the stop collar 18.

Figure 7:
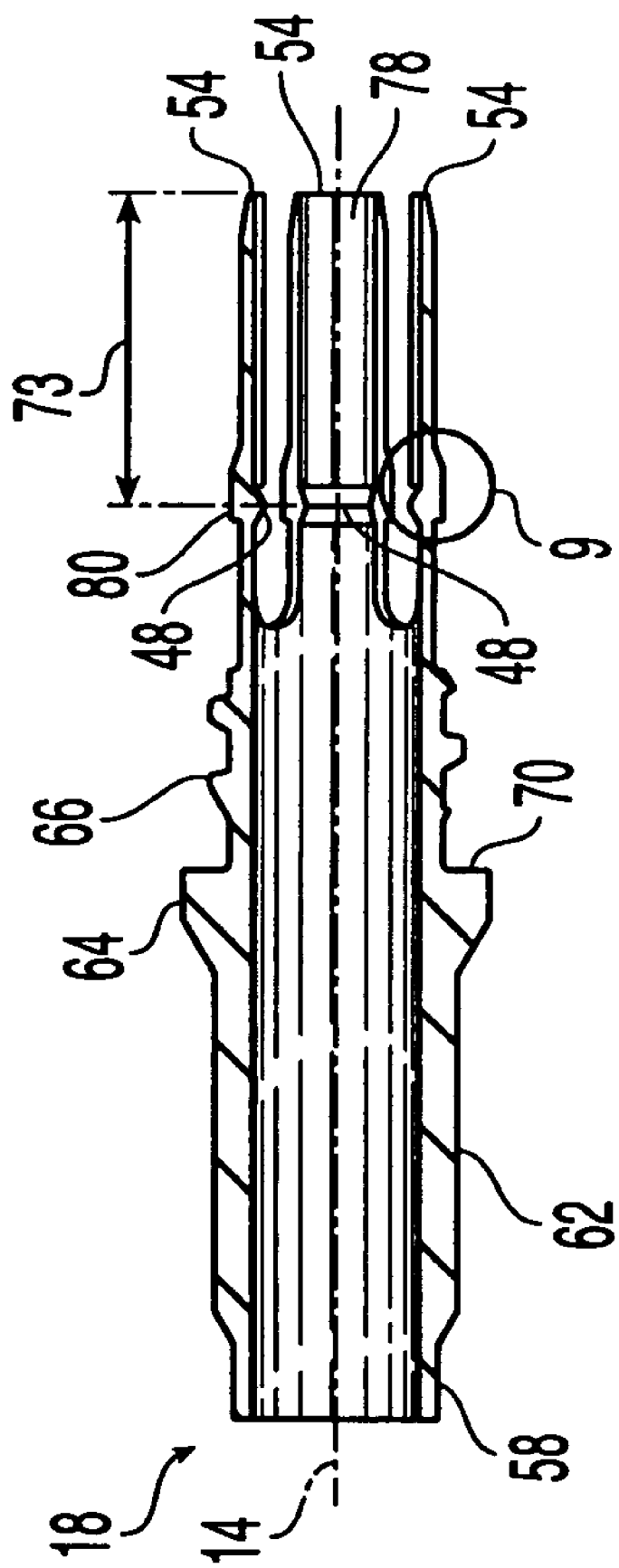
FIG. 7 shows a cross-sectional view along line 7-7 of FIG. 6.
Figure 9:
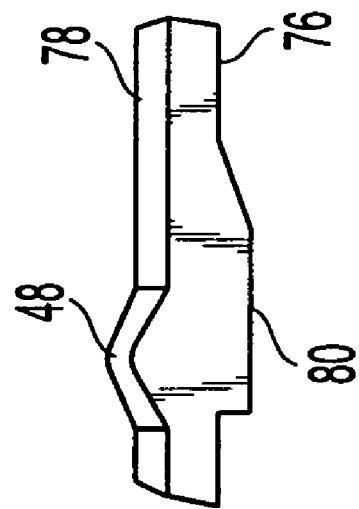
FIG. 9 shows an enlarged view of a nub and seating projection on the stop collar of FIG. 6.

As shown in FIGS. 7 and 9, the inner surface 78 of the fingers 68 may be smooth and may be configured and dimensioned to bear upon and slide along the shaft 22 of the self-drilling tap 12. The fingers 68 of the stop collar 18 may also be operably configured and dimensioned to selectively engage and disengage with the grooves 24 of the tap 12. For example, this may be accomplished by a projection, structure or nub 48 located on the inner surface 78 of each finger 68.

Figure 8:
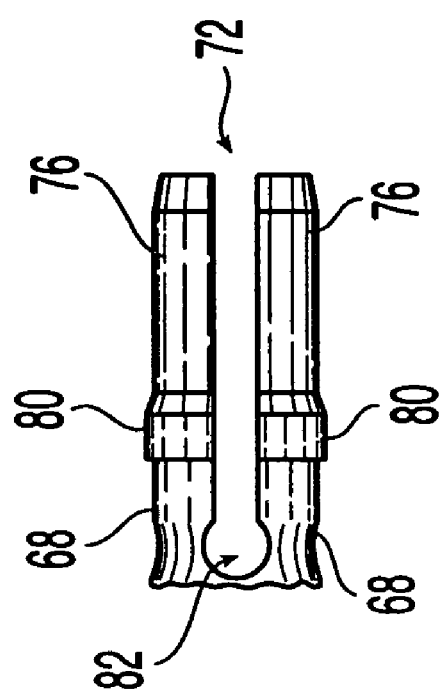
FIG. 8 shows an enlarged plan view of a slot of the stop collar of FIG. 6.

The outer surface 76 of each finger 68 may be configured and dimensioned to slidably receive the locking collar 20 over the outer surface 76. The outer surfaces 76 of the fingers 68 also may be configured and dimensioned to bear against the locking collar 20. This may be accomplished by a structure, as shown in FIGS. 8 and 9, such as a raised area or seat 80, located on the outer surface 76 of each finger 68. In general, as the locking collar 20 is advanced over the stop collar 18, the locking collar may press against the seat 80 and drive the nub 48 into engagement with a groove 24 on the shaft 22 of the self-drilling tap 12. The nub 48, for example, may be substantially triangular or trapezoidal in section. The shape of the nub 48 may be designed to securely engage with the groove 24 when locking the penetration or effective length 28 of the adjustable length tap assembly 10. The shape of nub may also be configured to facilitate disengagement of the nub 48 from a groove 24 when unlocking or adjusting the effective length 28 of the adjustable length tap assembly 10.

Referring to FIG. 8, the number and geometry of the slots 72 may be configured and dimensioned to provide the fingers 68 with special properties. For instance, a slot 72 comprising an enlarged rounded portion 82 at the base may be formed to provide special properties to the finger. The enlarged rounded portion 82 may provide increased flexibility while preventing stress concentrations and fatigue. Also, one or more slots 72 may be adapted to provide increased resiliency or flex to the fingers 68, making it easier to slide the stop collar 18 along the shaft 22, as the nubs 48 engage and disengage with the grooves 24.

The stop collar 18 may be formed from materials which are bio-compatible, and which are capable of withstanding the required mechanical loading and abrasion. For example, the stop collar 18, preferably may be made from materials that are durable and will prevent shearing of the nubs. In addition, the stop collar may be made from materials which provide the fingers with added resiliency to movement yet will not readily fatigue or fail during use. In addition, the stop collar 18 preferably may be made from materials which will not fail when placed into abrasive contact with a drill guide plate during use. Thus, for example, the stop collar 18 preferably may be made from any 300 series stainless steel. Preferably, 316 stainless steel may be used to form the stop collar 18. Other non-limiting examples of materials from which the stop collar may be formed in include titanium and titanium-alloys. The stop collar 18 might also be formed from materials which are non-magnetic in order to provide a tap assembly 18 which is suitable for use with an MRI system. The stop collar may also be radiolucent, or portions may be radiolucent.

Figure 11:
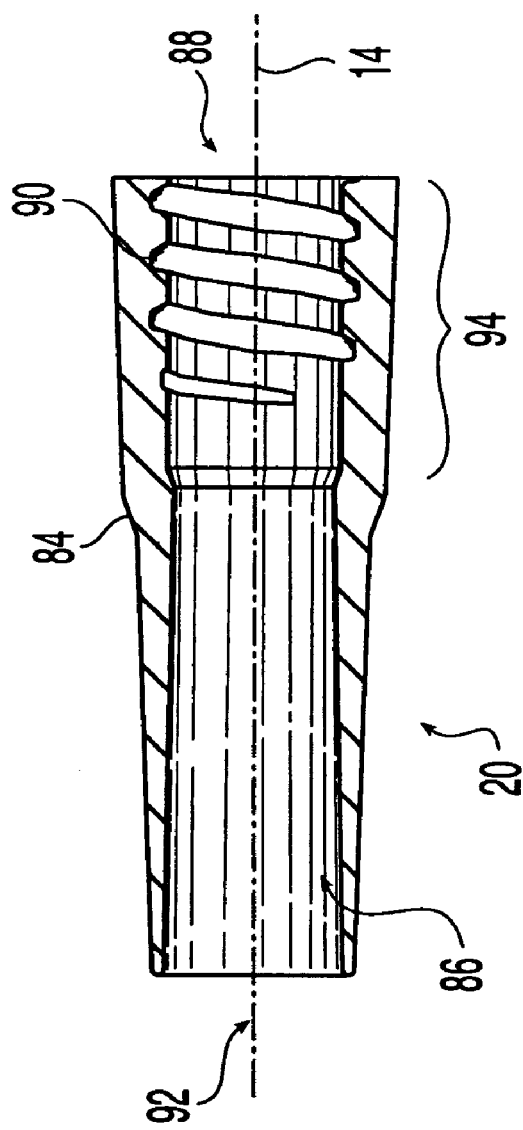
FIG. 11 shows a cross-sectional view along line 11-11 of FIG. 10.
Figure 10:
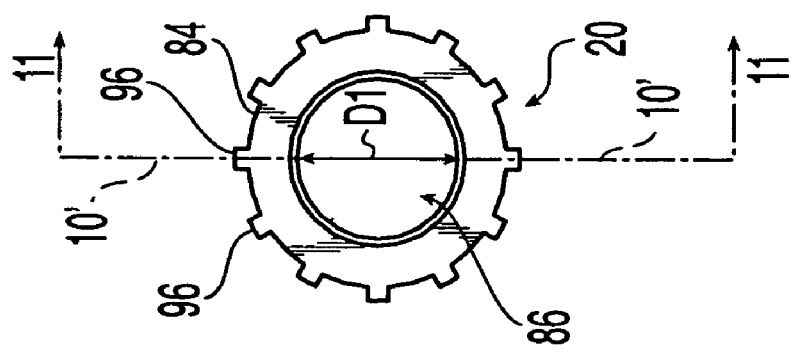
FIG. 10 shows a front elevation of the locking collar shown in FIG. 1.

Referring to FIGS. 10 and 11, the locking collar 20 generally comprises a tubular member having a bore 86, which is configured and adapted to engage or mate with the stop collar 18. The locking collar 20 may control the movement of the tap assembly. The cross-section of the locking collar 20 taken in a direction perpendicular to the longitudinal axis 14 of the locking collar may be substantially uniform. Alternatively, the locking collar 20 may have a cross section that varies. For example, the shape of the exterior surface 84 may be constant and the shape and diameter of the interior bore 86 may vary along the length of the locking collar. In another example, the shape of the exterior surface 84 may vary and the bore 86 may remain substantially unchanged along the length of the locking collar 20. In the embodiment shown in FIGS. 10 and 11, the locking collar is a generally hollow cylinder.

In general, the bore 86 of the locking collar 20 may be configured and dimensioned to slide along the tap 12 as well as over the fingers 68 of the stop collar 18. The cross-section of the bore 86 may be circular, polygonal or some other shape. In addition, the dimensions of the bore 86 may vary, and part of the bore 86 may be adapted to connect with the stop collar 18. For example, the distal end 88 of the bore 86 may comprise internal screw threads 90. Additionally, the bore 86 of the locking collar 20 may comprise sections having different dimensions. In particular, the locking collar may have a bore 86 comprising multiple sections of progressively smaller dimension. For instance, the dimensions of the bore may be greater at the distal end 88 than at the proximal end 92 of the locking collar 20, such that the progressive change in dimensions of the bore 86 presses the fingers 68 of the stop collar 18 more firmly into the grooves 24 of the shaft 22 when the locking collar 20 and stop collar 18 are coupled and tightened.

The exterior surfaces 84 of the locking collar 20 may also facilitate quick, reliable and accurate adjustment of the exposed tap length 28. In the embodiment of FIGS. 10 and 11, the dimension of the exterior surface 84 tapers gradually from the distal end to the proximal end. The locking collar 20 may be thicker at the distal end 88 to accommodate internal coupling elements 90 (for example, internal screw threads) which are adapted to engage or mate with connecting elements 66 (for example, external screw threads) on the stop collar 18. The locking collar 20 also may be thicker in the distal end 88 to provide a comfortable gripping section 94 so that the locking collar 20 may be reliably held and manipulated.

The exterior surface 84 of the locking collar 20 may further comprise raised areas 96 to enhance the grip and tactile feel of the locking collar 20. In addition, the raised areas 96 may promote the ease and reliability of setting and locking the length 28 of the tap assembly. In FIGS. 10 and 11, these raised areas 96 are in the form of longitudinal ridges that are radially disposed about the outer surface 84 of the locking collar. Other grip enhancing configurations on the exterior surface 84 might also be envisioned by one of ordinary skill in the art, such as for example, circumferential raised areas or ridges, or combinations of longitudinal and circumferential ridges, or other surface texturing.

The proximal end 92 of the locking collar 20 may have a thinner wall section than at the distal end 88 to enhance visibility through the locking collar 20 when looking at markings on the shaft 22. A thinner wall section may also enhance visibility through these areas of the locking collar 20. A relatively thin wall section at the distal end 88 may also enhance visual clarity along the shaft 22 and through openings or windows that may be formed in the locking collar 20. For instance, the proximal end 92 (i.e the finger tips) of the locking collar 20 may align with the selected length indicator 26 for a desired tap length 28. In another example, the selected tap length indicator 26 and indica 56 may be visible through an opening or window in an opaque locking collar 20.

In FIGS. 10 and 11, the proximal end 92 of the locking collar 20 may comprise a clear material, which may be substantially transparent. The visibility provided by such a material may allow a user to see directly through the locking collar 20 and easily view the length indicators 26, indica 56, and the proximal end 92 of the stop collar 18 to visually determine the effective length 28 of the adjustable-length tap assembly. The clear material may or may not have a tint. One clear material from which the locking collar may be made is plastic. In particular, the locking collar 20 may be configured and dimensioned to be fabricated as a molded piece. A locking collar 20 formed from plastic may have connecting elements 90 (for example, threads) for connecting to the stop collar 18 which may be made from other materials. In a preferred embodiment, the molded locking collar 20 may be made from a medical grade poly-carbonate. For example, the locking collar may be formed from "MAKROLON."™ In general, plastic materials that may be used for forming the locking collar 20 should be able to withstand gamma-sterilization during packaging. The locking collar 20 may also be made from other bio-compatible materials, including the same materials described above in connection with the shaft and stop collar.

Figure 12:
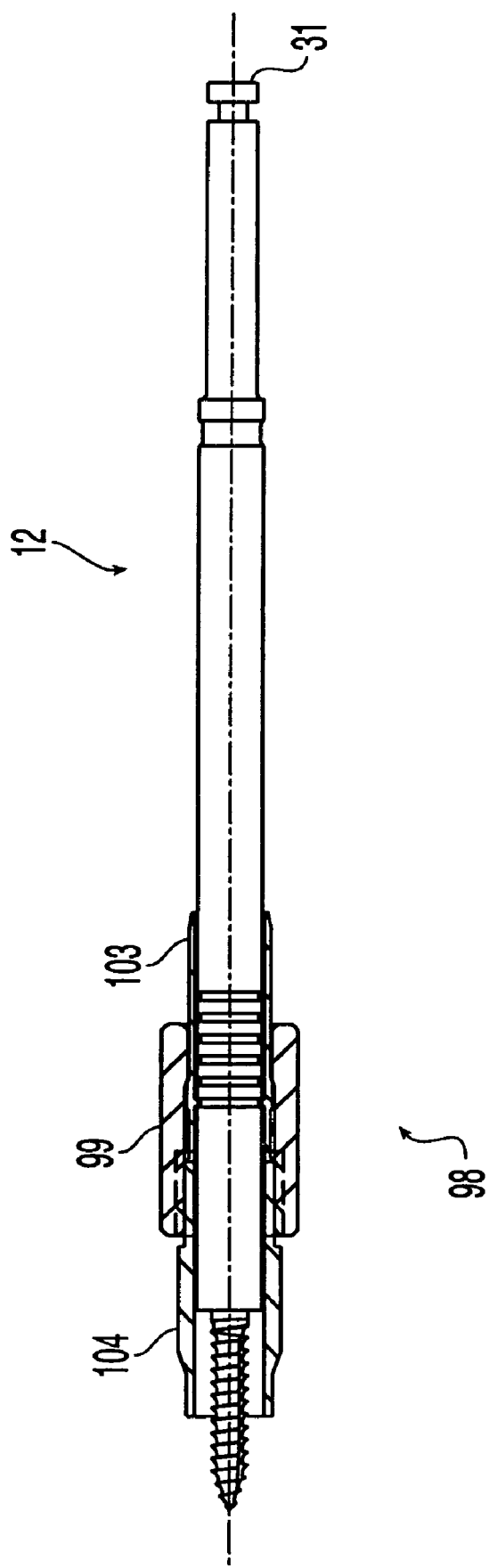
FIG. 12 shows a partial cross-sectional view along the longitudinal axis of another embodiment of the tap assembly of FIG. 1.
Figure 13:
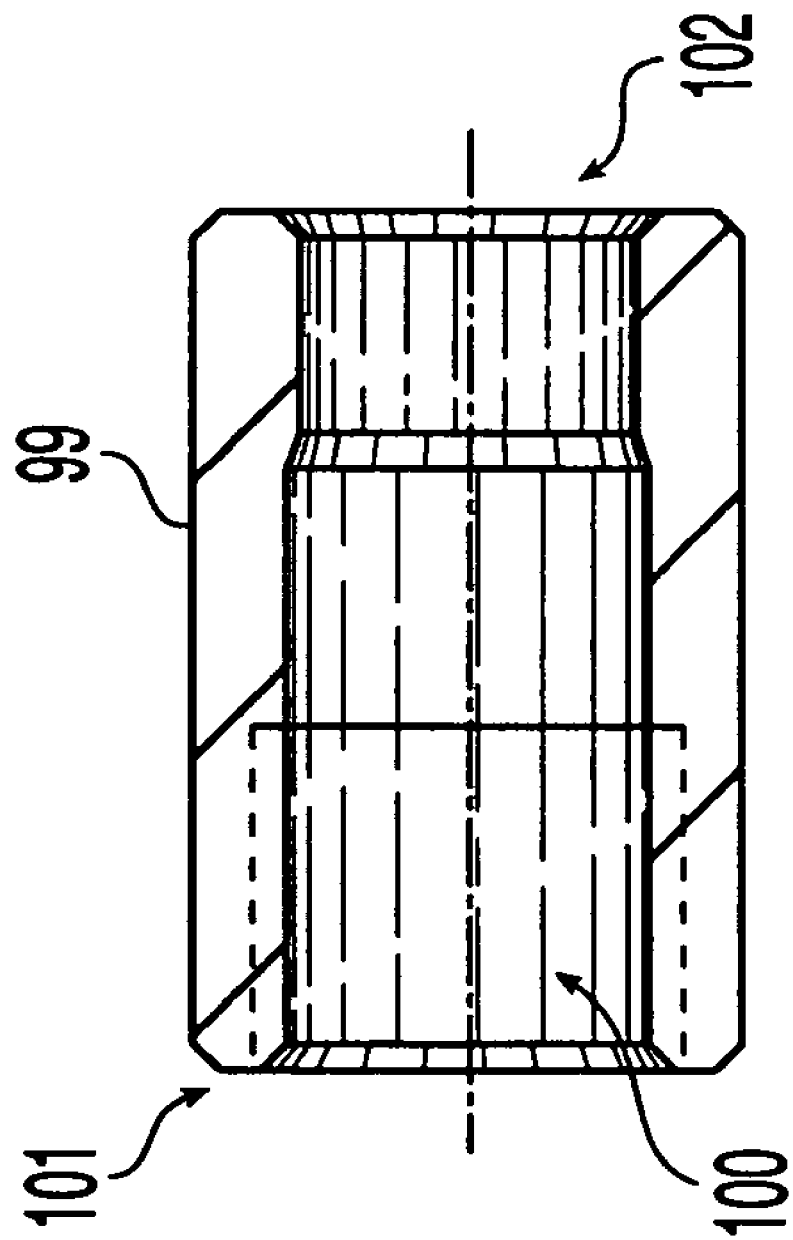
FIG. 13 shows a cross-sectional view of the locking collar along the longitudinal axis of the tap assembly of FIG. 12.

Referring to FIGS. 12 and 13, in another embodiment of the adjustable length tap assembly 98, the locking collar 99 may be specially configured and dimensioned to be formed from a metal-alloy such as 316 stainless steel. As shown in FIG. 13, the locking collar 99 may comprise a cylinder having a bore 100 of varying dimension, which extends from the distal end 101 to the proximal end 102. As shown in FIG. 12, the locking collar 99 may be capable of sliding completely over the proximal end 103 of the stop collar 104, when coupled to the stop collar, thereby providing an unobstructed view of the length indicators. Thus, the locking collar 99 may or may not have windows or slots to allow a user to read the setting of effective length 28 of the adjustable length tap assembly 98.

Figure 14:
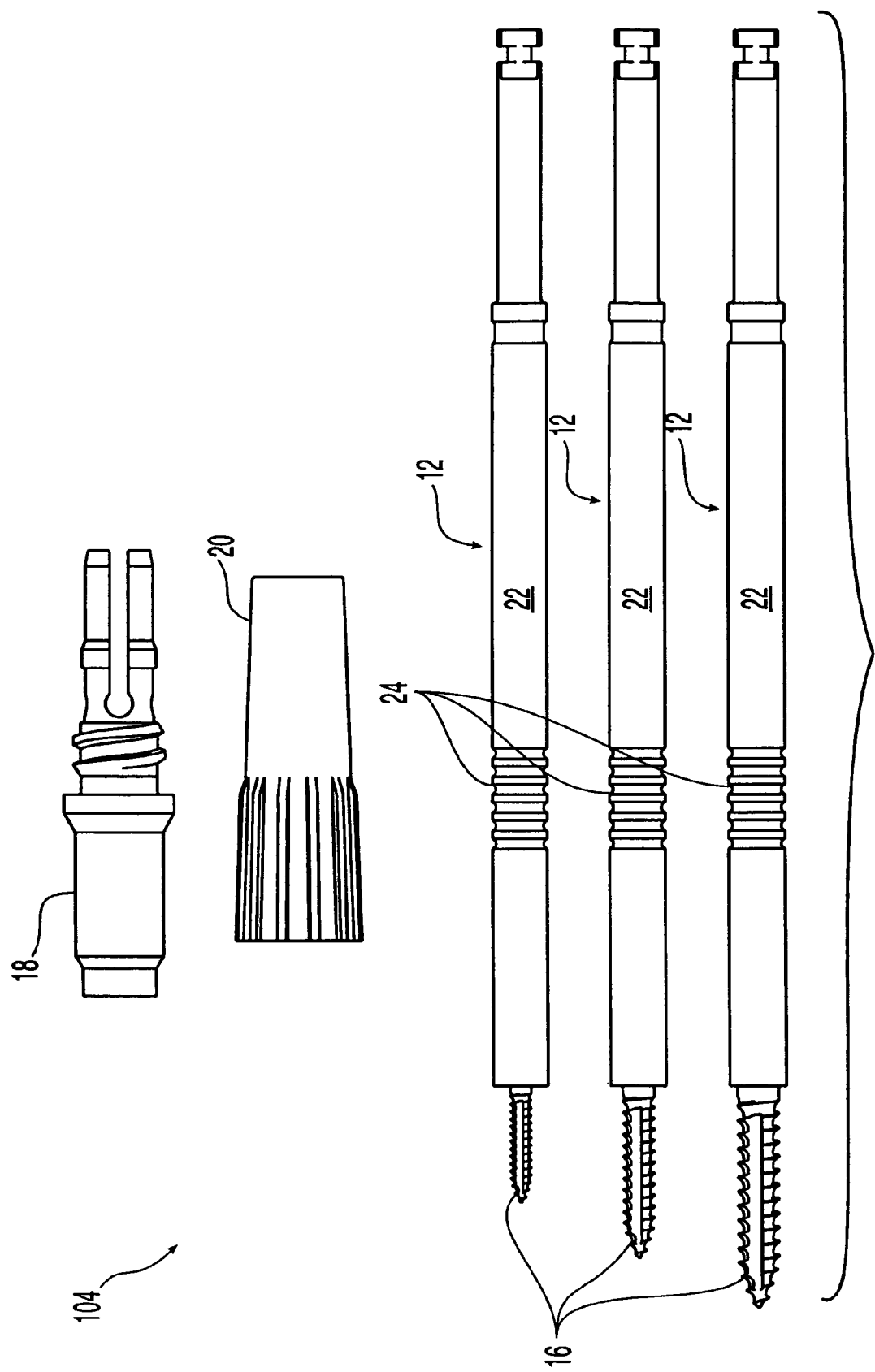
FIG. 14 is a perspective view of an exemplary collection of instruments, which in use, may form an adjustable length tap assembly of FIG. 1.
Figure 15:
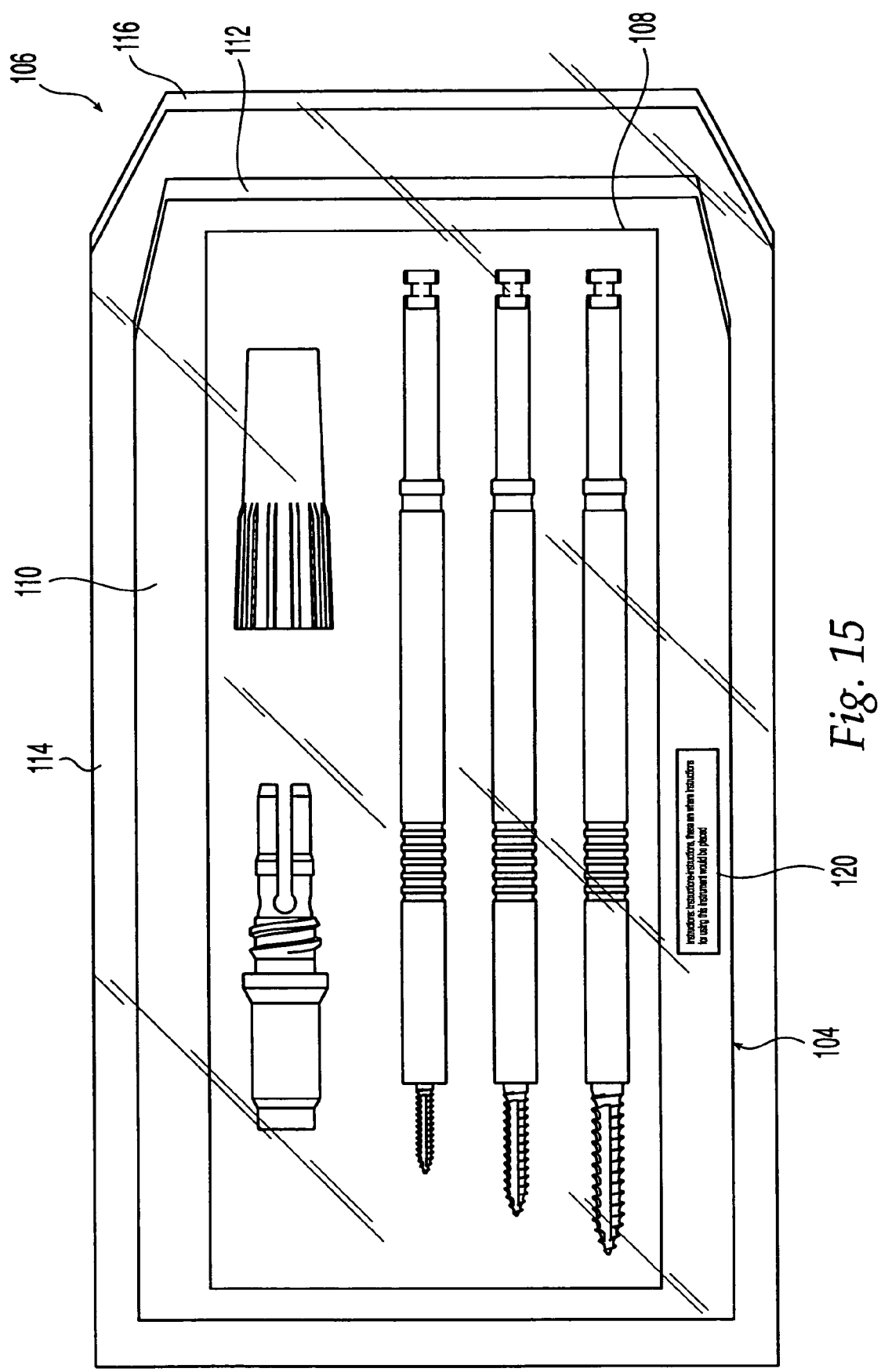
FIG. 15 is a plan view of an illustrative kit housing the collection of instruments of FIG. 14.

FIG. 14 shows an exemplary collection of instruments 104, which may be included in a pre-packaged surgical kit 106 (shown in FIG. 15) for forming an adjustable length tap assembly 12 that may be used to drill and tap bores in bone. The instruments 104 preferably may include a stop collar 18, a locking collar 20, and more than one tap 12. The collection of instruments 104 preferably may also include a handle (not shown) for releasably securing to each tap 12, so that a user may manually drill and tap bores in bone. In the illustrative embodiment shown in FIG. 14, three taps 12 are included in the collection 104. The taps 12 preferably may be used interchangeably with the stop collar 18 and the locking collar 20. The taps 12 preferably may also have identical shaft 22 and groove configurations 24. The taps 12 may further have cutting threads 16 that are adapted for screws of a similar type but of different diameter. Alternatively, the taps may have cutting threads 16 of substantially identical size and shape, or the cutting threads 16 adapted for different types of screws. It should be appreciated that a wide variety of various instruments may be contained in the kit 106. For example, a first kit may package a collection of instruments adapted for a particular mandible procedure, a second kit can package a collection of instruments adapted for a particular pelvic procedure, and a third kit may package a collection of instruments for a particular orthopedic procedure. FIGS. 14 and 15 illustrate one of many different possible embodiments for the instrument collection 104 and kit housing 106.

Referring to FIG. 15, in the illustrated embodiment, the kit 106 includes an interior tray 108 made, e.g., from die cut cardboard, plastic sheet, or thermo-formed plastic material. The tray 108 may include spaced apart tabs or the like (not shown), which may hold the various instruments 104 in a secure position during sterilization and storage prior to use. When packaged as a sterile assembly, the kit 106 may include an inner wrap 110, which is peripherally sealed by heat or the like, to enclose the tray 108 from contact with the outside environment. One end of the inner wrap may include a conventional peal-away seal 112, to provide quick access to the tray 108 at the instant of use, which preferably occurs in a sterile environment, such as within an operating room. When packaged as a sterile assembly, the kit 106 may also include an outer wrap 114, which is also peripherally sealed by heat or the like, to enclosed the inner wrap 110. One end of the outer wrap may also include a conventional peal-away seal 116, to provide access to the inner wrap 110 and its contents. The outer wrap 114 can be removed from the inner wrap in anticipation of imminent use, without compromising sterility of the contents of the kit 106.

Each inner and outer wrap 110 and 114 may include a peripherally sealed top sheet 118 and bottom sheet (not shown). In the illustrated embodiment, the top sheet 118 preferably may be made of transparent plastic film, like polyethylene or MYLAR.™ material, to allow visual identification of the contents of the kit 106. The bottom sheet may be made from a material that is permeable to ETO sterilization gas, such as, for example, TYVEK™ plastic material. The kit 106 may also include in the tray 108 directions 120 for using the contents of the kit 106 to carry out a desired procedure. An exemplary procedure which the directions 120 can describe will be explained later. When packaged as a sterile assembly, the directions 120 may also include a statement, for example, "For Single Patient Use Only" (or comparable language) to affirmatively caution against reuse of the contents of the kit 106 whose performance characteristics and efficacy may degrade after use. The adjustable length tap assembly 20, for these reasons, may be used but for a single surgical procedure and then discarded. The directions 120 may also affirmatively instruct against resterilization of a portion or all of the contents of the kit 106, and also may instruct the physician to dispose of at least these contents of the kit 106 upon use in accordance with applicable biological waste procedures. The presence of the collection of instruments 104 packaged in the sterile kit 106 may verify to the physician that the contents are sterile and have not been subjected to prior use. The physician may thereby be assured that the instruments 104 meet established performance and sterility specifications.

In use, the locking collar 20 slips over the stop collar 18 and tap 12 and when tightened to the stop collar 18, locks the assembly 10. The locking may be accomplished by nubs 48 on the fingers 68 of the stop collar 18 being driven into grooves 24 on the shaft 22. The proximal edge of the fingers (i.e., the finger tips) 88 may align with the length indicator 26 on the tap shaft 12 that corresponds with the groove 24 the nubs 48 engage. Once the stop collar 18 and the locking collar 20 are coupled together, the degree of engagement between the nubs 48 and the locking grooves 20 may be controlled. The degree of engagement between the grooves 24 and the nubs 48 may vary by design from a firm engagement to loose engagement. When loosely engaged the stop collar 18 and the locking collar 20 may be moved in unison along the shaft 22 in a ratchet like fashion. To promote a secure connection between the stop collar 18, the locking collar 20, and the shaft 22, the fingers 68 of the stop collar 18 have a raised area 80 on the outer surface 76 to cause the nub 48 on the inner surface 78 to be pushed firmly into engagement with the groove 24. The stop collar 18 and locking collar 20 preferably are capable of resisting, without axial movement, an axial force of at least about 300 N, when the adjustable length tap assembly is locked.

The adjustable length tap assembly 10 is directed toward a method for drilling and tapping holes in bone. Initially, a user selects a tap 12 for preparing a bore which is adapted for a particular screw configuration. The selection may be based, for instance, on the screw diameter, or the part number of the screw. A stop collar 18 then may be mounted about the tap 12 along a shaft 22, with the proximal ends 54 of the fingers 68 pointing toward the proximal end 31 of the shaft 22. A locking collar 20 may then be positioned on the shaft 22 of the tap 12 so that it is capable of coupling with the stop collar 18. The stop collar 18 and the locking collar 22 are then joined together.

The tightness of the connection between the stop collar 18 and the locking collar 20 may then be adjusted to provide a desired resistance to movement between the stop collar-locking collar combination and the tap 12. The position of the stop collar 18 may then be adjusted to a desired tap length 28 setting by aligning the proximal ends 74 of the stop collar with the desired length indicator 26. For example, the numeral 5 may designate the appropriate length indicator 26 for a particular screw with a length of 5 mm. The connection between the stop collar 18 and the locking collar 20 may then be tightened to secure the selected length 28 of the tap assembly. Alternatively, the position of the stop collar may be positioned to provide a desired tap length. The stop collar 18 may be advanced to set the desired position and the locking collar then positioned on the shaft, coupled to the stop collar, and adjusted to lock the stop collar and locking collar assembly in place on the shaft.

The proximal end 31 of the self-drilling tap 12 may then be inserted in to a drill (not shown), such as a battery powered reversible drill. The tip 13 of the self-drilling tap 12 may be seated in a guide plate and placed into contact with bone. The drill may then be used to rotate the adjustable length tap assembly 10 to bore and tap a hole of predetermined dimension into the bone. The maximum depth of the bore may be reached when the nose 58 of the stop collar contacts the guide plate. The adjustable length tap assembly 10 may then be withdrawn from the bore and the guide plate, and a screw advanced and secured in the tapped bore.

The locking mechanism of the assembly 10 allows the stop collar 18 and locking collar 20 to rotate with respect to the tap 12, particularly after the stop collar 18 hits the drill guide plate without affecting the previously adjusted length setting 28. Because the nub 48 is firmly seated in the groove 24, the length of the tap 28 may not change, however, the stop collar 18 and locking collar 20 are free to rotate about the shaft 22. This may facilitate accuracy in the advancement of bores having a pre-selected depth. For instance, if relative rotation between the stop collar 20 and the shaft could change the length of the exposed cutting threads 28, each time the stop collar hits the drill guide plate the resulting movement between the shaft and the stop collar might potentially cause the tap 12 to change length 28. If the exposed length of the cutting threads 28 was unintentionally lengthened the bore might proceed undesirably through the bone and into adjacent tissue. By contrast, if the exposed length of the cutting threads 28 was decreased, a screw advancing into untaped bone might damage or crack the bone or in the case of resorbable screws, damage may occur to the screw.

The tap assembly may also provide useful tactile feed back to the user, due to the ratchet effect of the nubs 48 engaging and disengaging with the grooves 24 as the stop collar 18 and locking collar 28 are moved along the shaft 22. A user may feel and hear the number of clicks as the nubs disengage and engage grooves as the stop collar translates along the shaft from a first known tap length setting to a desired second tap length setting, thereby increasing the speed of tap adjustments during a procedure. In addition, the ratchet effect of the locking mechanism may provide an additional check for assuring the proper length is selected as the user need not rely on a purely visual system to select or check the length adjustment of the tap assembly.

While the above adjustable length tap assembly has been described with reference to certain preferred embodiments, it should be kept in mind that the scope of the present invention is not limited to these embodiments. For instance, the adjustable length tap assembly may be modified or extended to accommodate particular formulations of construction materials or fabrication techniques which may require different connecting elements. Similarly, the number and spacing of the grooves on the shaft may be changed to accommodate different screw lengths. Also, different materials and surface coatings, or outer layers of different materials may be applied to the adjustable length tap assembly. In addition, the embodiments above can be modified so that some features of one embodiment are used with the features of another embodiment. One skilled in the art may adapt variations of these preferred embodiments which, nevertheless, fall within the spirit of the present invention, whose scope is defined by the claims set forth below.

What is claimed is:

1. A method for drilling and tapping a threaded bore in bone comprising:
   selecting a self-drilling tap having a longitudinal axis and cutting threads on a distal end of the tap;
   positioning a stop collar on the tap, the stop collar configured to lockingly engage the tap;
   coupling a locking collar to the stop collar;
   sliding the stop collar along the longitudinal axis of the tap to a user selectable position;
   locking the stop collar to the tap at the desired position to set an effective penetration length for the cutting threads;
   drilling a threaded bore into the bone with the cutting threads on the tap; and
   contacting the stop collar against a surface to limit the penetration depth of the tap into the bone; and
   rotating the stop collar with respect to the tap while the stop collar is locked at the desired position when the stop collar contacts against the surface.

2. The method of claim 1, wherein the step of coupling the locking collar to the stop collar comprises passing at least a portion of the locking collar over the stop collar.

3. The method of claim 1, wherein the step of coupling the locking collar to the stop collar comprises engaging threads disposed on an external surface of the stop collar with threads disposed on an internal surface of the locking collar.

4. The method of claim 1, wherein the step of locking the stop collar to the tap comprises releaseably engaging an internal surface of the stop collar with the tap.

5. The method of claim 4, wherein the step of engaging the internal surface of the stop collar with the tap comprises engaging a projection on the internal surface with a groove on the tap.

6. The method of claim 5, wherein the projection is disposed on a flexible finger of the stop collar, the step of engaging the projection with the groove of the tap comprising deflecting the finger towards the tap with the locking collar.

7. The method of claim 1, wherein the step of drilling a threaded bore into the bone comprises rotating and advancing the tap into the bone.

8. A method for drilling and tapping a threaded bore in bone comprising:
    selecting a self-drilling tap having a longitudinal axis and cutting threads on a distal end of the tap;
    positioning a stop collar and locking collar on the tap in any order, the stop collar configured and adapted to lockingly engage the tap;
    connecting the locking collar with the stop collar, the connection between the two collars being adjustable in tightness;
    sliding the stop collar along the longitudinal axis of the tap to a user selectable position;
    tightening the locking collar on the stop collar;
    engaging the stop collar with the tap at the selected position, thereby setting an effective penetration length for the cutting threads;
    drilling a threaded bore into the bone with the cutting threads on the tap;
    contacting the stop collar against a surface to limit the penetration depth of the tap into the bone; and
    rotating the stop collar with respect to the tap while the stop collar is locked at the set penetration depth when the stop collar contacts against the surface.

9. The method of claim 8, further comprising a step of varying the tightness between the locking collar and stop collar to adjust resistance to sliding between the stop collar-locking collar combination and the tap.

10. The method of claim 8, wherein the drilling step comprises rotating the tap into the bone.

11. The method of claim 10, wherein the stop collar-locking collar combination is independently rotatable with respect to the tap, and further comprising a step of stopping rotation of the stop collar-locking collar combination when the stop collar contacts the surface.

12. The method of claim 8, wherein the step of connecting the locking collar to the stop collar comprises engaging threads disposed on an external surface of the stop collar with threads disposed on an internal surface of the locking collar.

13. The method of claim 8, wherein the step of engaging the stop collar with the tap comprises releaseably engaging an internal surface of the stop collar with the tap.

14. The method of claim 13, wherein the step of engaging the internal surface of the stop collar with the tap comprises engaging a projection on the internal surface with a groove on the tap, the stop collar being rotatable with respect to the tap without movement along the longitudinal axis of the tap.

15. The method of claim 14, wherein the projection is disposed on a flexible finger of the stop collar, the finger being deflectable in response to adjusting the tightness between the stop collar and locking collar.

16. A method for drilling and tapping a threaded bore in bone comprising:
    selecting one each of the following:
        a self-drilling tap including a shaft defining a longitudinal axis, cutting threads disposed on a distal end of the shaft, and a plurality of external circumferential grooves on the shaft;
        a stop collar including at least one elastically deformable finger configured and adapted for releaseably engaging the grooves on the tap;
        a locking collar adapted and configured to couple with the stop collar;
    connecting the locking collar with the stop collar on the shaft of the tap;
    sliding the stop collar along the longitudinal axis of the tap to a user selectable position;
    engaging the at least one finger of the stop collar with at least one of the grooves of the tap at the desired position to set an effective bone penetration length for the cutting threads;
    locking the finger in the at least one groove of the tap;
    drilling a threaded bore into the bone with the cutting threads on the tap; and
    contacting the stop collar against a surface to limit the penetration depth of the tap into the bone; and
    rotating the stop collar with respect to the tap while the finger is engaged with the at least one groove when the stop collar contacts against the surface.

17. The method of claim 16, wherein the step of connecting the locking collar to the stop collar comprises engaging threads disposed on an external surface of the stop collar with threads disposed on an internal surface of the locking collar.

18. The method of claim 16, wherein the step of engaging the finger of stop collar with groove of the tap comprises engaging a projection on an internal surface of the finger with the groove.

19. The method of claim 16, wherein the tightness of the connection between the stop collar and locking collar is adjustable, the finger of the stop collar being inwardly deflectable in response to adjusting the connection tightness, and wherein the step of locking the finger in the groove comprises tightening the locking collar to the stop collar.

20. A method for drilling and tapping a threaded bore in bone comprising:
    selecting a self-drilling tap having a longitudinal axis and cutting threads on a distal end of the tap;
    positioning a stop collar on the tap, the stop collar adapted and configured to lockingly engage the tap;
    sliding the stop collar along the longitudinal axis of the tap to a user selectable position;
    viewing a length indicator of a user selectable position through at least a transparent portion of a locking collar;
    tightening the locking collar on the stop collar;
    engaging a flexible inner surface of the stop collar with the tap at the selected position to set an effective penetration length for the cutting threads;
    drilling a threaded bore into the bone with the cutting threads on the tap; and
    contacting the stop collar against a surface to limit the penetration depth of the tap into the bone.

21. The method of claim 20, wherein the inner surface of the stop collar is movable inwards in response to tightening the locking collar.

22. The method of claim 20, wherein the step of tightening the locking collar on the stop collar comprises engaging threads disposed on an external surface of the stop collar with threads disposed on an internal surface of the locking collar.

23. The method of claim 20, wherein the step of engaging the inner surface of the stop collar with the tap comprises engaging a projection on the inner surface with a groove on the tap.

24. The method of claim 20, wherein the inner surface of the stop collar is disposed on a flexible finger that is movable inwards in response to tightening the locking collar; and wherein the step of engaging the inner surface with the tap comprises deflecting the finger towards the tap by tightening the locking collar.

* * * * *

UNITED STATES PATENT AND TRADEMARK OFFICE
CERTIFICATE OF CORRECTION

PATENT NO. : 7,569,058 B2 Page 1 of 1
APPLICATION NO. : 11/221546
DATED : August 4, 2009
INVENTOR(S) : Zwirnmann It is certified that error appears in the above-identified patent and that said Letters Patent is hereby corrected as shown below:

In column 1, line 11, delete "Bone,"which" and insert -- Bone," which --, therefor.

In column 2, line 65, after "further include" delete "include". (Repeated Occurrence)

In column 3, line 27, delete "self drilling" and insert -- self-drilling --, therefor.

In column 12, line 57, in Claim 1, after "tap;" delete "and".

In column 14, line 23, in Claim 16, after "tap;" delete "and".

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,569,058 B2 Page 1 of 1
APPLICATION NO. : 11/221546
DATED : August 4, 2009
INVENTOR(S) : Ralph Fritz Zwirnmann It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 715 days.

Signed and Sealed this

Seventh Day of September, 2010

David J. Kappos
*Director of the United States Patent and Trademark Office*